(12) United States Patent
Selker et al.

(10) Patent No.: US 8,008,065 B2
(45) Date of Patent: Aug. 30, 2011

(54) DISPOSABLE BIOREACTOR VESSEL PORT

(75) Inventors: Mark Selker, Los Altos Hills, CA (US);
Timothy Johnston, Eureka, CA (US);
Barbara Paldus, Woodside, CA (US)

(73) Assignee: Finesse Solutions, LLC., San Jose, CA (US)

( * ) Notice: Subject to any disclaimer, the term of this patent is extended or adjusted under 35 U.S.C. 154(b) by 1191 days.

(21) Appl. No.: 11/728,560

(22) Filed: Mar. 26, 2007

(65) Prior Publication Data
US 2008/0032389 A1    Feb. 7, 2008

Related U.S. Application Data

(60) Provisional application No. 60/835,329, filed on Aug. 2, 2006.

(51) Int. Cl.
*C12M 1/34* (2006.01)
*C12M 1/26* (2006.01)
*G01N 1/10* (2006.01)

(52) U.S. Cl. ............... 435/287.1; 435/288.7; 435/289.1; 435/309.2; 73/863.81; 73/863.85

(58) Field of Classification Search ............... 435/287.1, 435/289.1, 304.1, 288.7, 309.2; 73/863.81, 73/863.85
See application file for complete search history.

(56) References Cited

U.S. PATENT DOCUMENTS

| | | | | |
|---|---|---|---|---|
| 4,163,903 | A | * | 8/1979 | Robertson ..................... 250/554 |
| 4,353,488 | A | * | 10/1982 | Schneiter et al. ............. 222/501 |
| 7,434,448 | B2 | * | 10/2008 | Weyl et al. ................... 73/23.31 |
| 2005/0239198 | A1 | * | 10/2005 | Kunas et al. ............... 435/297.1 |

FOREIGN PATENT DOCUMENTS

WO   WO 2004109270 A1 *  12/2004
WO   WO 2005068059 A1 *   7/2005

* cited by examiner

*Primary Examiner* — William H Beisner
(74) *Attorney, Agent, or Firm* — Herbert Burkard

(57) ABSTRACT

A port for use with a bioreactor vessel comprising:
i) a base member comprising a hollow tubular portion and a base plate configured to be sealingly affixed to a hole in the wall of a bioreactor vessel
ii) a hollow, generally tubular bushing member for containing electrical, optical, microfluidic and/or chemical monitoring components which bushing member fits inside the bore of the tubular portion of the base member, both the base member and bushing member providing access to the contents of a bioreactor by;
iii) a monitoring assembly inserted into the bushing member which assembly comprises means for providing incoming optical and/or electrical signals and means for collecting and transmitting measurement signals resulting from the interaction of incoming optical and/or electrical signals with the contents of a bioreactor; and
iv) a cover which maintains the position and alignment of components ii) and iii) relative to the base member.

9 Claims, 9 Drawing Sheets

DISPOSABLE BIOREACTOR VESSEL PORT

This application claims priority from Provisional Application 60/835,329 filed Aug. 2, 2006, the disclosure of which application is incorporated herein by this reference.

FIELD OF THE INVENTION

This invention is directed to an improved port for bioreactor vessels. The port can be used to enable the insertion of instruments for monitoring the conditions inside the bioreactor vessel and/or for the introduction of micro-organisms, nutrients or reagents into the vessel.

BACKGROUND OF THE INVENTION

A bioreactor can be defined as a vessel in which a biological conversion is effected. This definition can apply to any conversion involving enzymes, micro-organisms, or animal or plant cells. However, we will use the word bioreactor to refer to vessels (usually made of glass, metal or a polymer) in which organisms are cultivated in a controlled manner. Modern cell cultivation is typically accomplished using a bioreactor or a fermentor vessel. Despite the fact that a bioreactor and a fermentor are essentially similar in design and general function, the dichotomy in nomenclature is sometimes used to distinguish between animal and plant cell culture. Herein we will use the term bioreactor in an inclusive, generic sense as including both aerobic and anerobic cultivation of both microbial, animal and plant cells, and thus encompassing a fermentor.

The goal of an effective bioreactor is to control, contain and positively influence a desired biological reaction. One desired biological reaction considered here is the growth of microorganisms. The most popular method for accomplishing this is a batch cultivation system. See, for example, James Lee, *Biochemical Engineering*, Washington State University, e-book, 2002. For simplicity and clarity we will detail a batch biological process here, but it is to be understood that the port design of the present invention is applicable to any bioreactor process (e.g.: perfusion or other continuous process) and also to a chemical process where monitoring of the reaction vessel is important.

In a batch biological process the microorganisms are inoculated into a culture medium and the growth cycle commences. This growth cycle consists of:
1. Lag phase: A period of time during which the cells have not yet commenced significant growth.
2. Accelerated growth phase: The period during which the number of cells increases and the cell division rate reaches a maximum.
3. Exponential growth phase: The period during which the number of cells increases exponentially as the cells divide. The growth rate is increasing during this phase, but the division rate is constant and at its maximum.
4. Decelerated growth phase: After the growth rate reaches a maximum it is followed by a deceleration in both the growth rate and division rate.
5. Stationary phase: The cell population reaches a maximum value and does not increase further.
6. Death phase: After the nutrients available for the cells are depleted and/or the bioreactor environment becomes too hostile, cells will start to die and the number of viable cells will decrease.

Generally, it is desirable to minimize the lag phase, ensure adequate nutrient concentration (e.g.: glucose) in the growth phases, and to delay the onset of the cell death phase as long as possible. In order to accomplish this optimization of the biological reaction, i.e., specifically in order to maximize the yield of product from a bioreactor, two factors must be considered. The first is providing suitable reactor design parameters for the particular biological, chemical, and physical aspects of the system. The second area of major importance in bioreactor design is monitoring the conditions inside the reactor so as to control the parameters relevant to micro-organism growth. These parameters can include, but are not necessarily limited to:
1. Temperature
2. pH
3. Dissolved gasses (e.g.: $O_2$, $CO_2$,)
4. Nutrients (e.g.: sugars such as glucose, proteins, amino acids, fats)
5. Inorganic Salts
6. Water and foam levels in the bioreactor
7. Product formation (e.g., cholesterol, vitamins)
8. By-product removal (e.g.: lactic acid, $NH_3$)
9. End products: e.g., enzymes and proteins
10. Cell density (concentration)
11. Cell viability
12. Conductivity and osmolality It should be noted that many of these parameters are critical irrespective of which method of cultivation (i.e., batch, continuous, or perfusion) is used, and that some parameters are more important than others depending on the type of microbe or cell being grown. The process can, for example, be a batch process in a stirred tank, a perfusion process or can utilize an airlift bioreactor etc. However, knowledge of the parameters that relate to cell growth, cell respiration, cell death, and yield maximization, are critical to understanding and optimizing any growth process.

Due to the requirements for handling hydrostatic pressure and the pressure associated with cleaning/sterilization procedures, bioreactors have heretofore generally been constructed of stainless steel such as 316L, sometimes including glass components. The initial cost of a 316L stainless steel bioreactor and the concomitant plumbing is substantial. The cost to run the impeller, the aerator, and to cool/heat the bioreactor is also sizable. Finally, the costs of cleaning and sterilizing such a reactor after use, and disposing of the waste water from the cleaning process are non-negligible. Given the aforementioned costs associated with running a conventional steel bioreactor, many organizations have begun using disposable bioreactors. These single use bioreactors are generally constructed using films which have been proven to be biocompatible and animal derived component free. Often these films must comply with standards set by both the U.S. Food and Drug Administration (FDA) and the United States Pharmacopeia (USP). The layer in contact with the media is often polyethylene or ethylene-vinyl acetate (EVA), and the outer (reinforcing) layer is often nylon, though many different combinations of materials and construction techniques have been used or, at least, proposed. Variations in the materials utilized are frequently determined by the precise mixing implementation, and/or on whether or not the bag needs to be gas permeable. Often these disposable bag reactors include gas inlet and outlet ports, inlet and outlet filters, a pressure control valve, and a port to fill the bag with aqueous media.

Given the many variations in disposable bioreactor design, there are also many variations in the methods for accomplishing mixing and aeration. One popular design for bag style bioreactors uses a platform that implements a rocking motion to the bag in order to mix and aerate the bag contents (see e.g., Published U.S. Pat. No. 6,190,913). Other disposable bioreactor designs look more like conventional stainless steel and glass reactors, and use impellers that essentially mimic the mixing methods used in conventional steel and glass bioreactors (see for example U.S. Patent Application 2005/0239199A1). Many claims are made on both sides of this issue regarding the efficacy of the various mixing methods. The rocking motion allegedly is gentler than the use of impellers and therefore leads to less damage to mammalian cells but apparently can stress the seams of the bag and may not always provide sufficiently effective mixing and/or oxygenation. The impeller based designs are generally more effective agitators, but can sometimes damage cells, and also require more infra-structure.

Irrespective of the method used for mixing in disposable bioreactors, it is clear that suitable methods for determining the efficacy of the bioreactor process and reliable methods for obtaining timely information on the status of the process are lacking. Only recently have many of the leading disposable bioreactor manufacturers attempted to marry sensor technology with their bag. The general ambiguity regarding the efficacy of the mixing and oxygenation in disposable bioreactor bags highlights the fundamental need to be able to monitor critical process parameters. Current practice with standard glass and steel bioreactors is to introduce the applicable probes through a port in the reactor wall or head plate. The use of such a port allows the calibration and testing of the probes before placing the probes into the bioreactor. However, with disposable bioreactors it is difficult to measure many of the aforementioned critical parameters using most of the currently available probes due to the dielectric nature of disposable bioreactor bags. Specifically, most existing electro-chemical probes used to measure reaction parameters such as dissolved oxygen, pH, and dissolved $CO_2$ require the probe to be both shielded and grounded. Achieving this is often complicated by the lack of a metal or at least a conductive housing for a disposable (and hence dielectric) bag bioreactor. Additionally, many of the traditional probes are too large or otherwise not functionally useable in disposable bag bioreactors.

One method of avoiding many of the issues inherent with traditional electrochemically based sensors in polymeric bioreactor bags is through the use of different transduction methodologies. For example, probes for measuring dissolved oxygen, pH, and dissolved CO2 utilizing optical based sensing technologies have recently become available. Different methods have been reported for integrating the optical sensors in a disposable bioreactor bag. One possible method is to seal a patch having a probe mounted on it directly into the bag (See Published U.S. Patent Application: 2005/0272146). Shown in FIG. 1 is a disposable bag as described in the above-cited patent application, where 206 is the location for the probes which are to be attached to the inside of the bag. The patch needs to be assembled into the bag using bio-compatible materials which can endure gamma radiation or alternative methods of sterilization. Though not entirely clear from the Figures of the above-cited patent application, it is possible to mount "dots" containing a dye sensitive to a target analyte (e.g., pH, or dissolved $O_2$ or $CO_2$,) on the inside surface of a patch of bio-compatible plastic and use an RF or thermal source to fuse this patch into the bag wall. The dots on this patch can contain various fluorescent materials for use in sensing pH, dissolved $O_2$, and dissolved $CO_2$. These dots generally utilize a "dye"e.g., a transition metal complex whose fluorescence lifetime is quenched by the presence of the target analyte to be measured. The material can be printed onto the patch or attached using a decal. The only requirements are that sufficient light to excite the dye present on the inside surface of the patch is transmitted through the patch window, and that sufficient fluorescence signal is transmitted back out through the window such that the decay in the signal strength can be monitored from outside the bag. The monitoring or interpretation of the signal is typically done at the transmitter which houses the user interface, the signal processing, and in some instances the opto-electronic components of the analyte monitoring system.

In the case of disposable bag reactors utilizing a patch of material fused into the lining, or simply using the disposable reactor lining itself to mount optically based probes significant limitations arise in that it is difficult to bring high fidelity optical probes or intrusive optical connections into and out of the bag. Using a simple dot affixed to the inside of the disposable bioreactor wall, only optical signals of limited fidelity can be transmitted back and forth. This puts greater requirements and restrictions on the optics and electronics in the transmitter. Furthermore, the materials used to make the bags are typically chosen for bio-compatibility, gas permeability, and strength, rather than for optical transparency. This makes bringing in high fidelity optical signals problematic as the light may be attenuated and/or randomly scattered as it passes through the wall of the bag. It also makes it difficult or even impossible to optimize the efficiency of the optical delivery and collection system.

Other issues which arise from relying on the relatively simple technique of affixing a sensor material to the inside of a disposable bioreactor bag wall are that it can preclude the installation of more advanced sensors. Specifically, as sensors continue to advance it is clear that signals in addition to an optical signal will need to be passed into and out of the bioreactor. It is likely that when sensors utilize optical, electrical, chemical, acoustic, magnetic, and micro-fluidic technologies or a subset of these technologies, more communication with outside instrumentation will be necessary than is possible using currently available techniques.

Through the use of a more sophisticated interface or window into the bioreactor, multiple measurements can be simultaneously accomplished. These measurements can include any of the parameters discussed above. The measurement methods include, but are not limited to those that are based on optical, electrical, chemical, bio-chemical, acoustic, magnetic, and micro-fluidic techniques, or any combination thereof. These techniques can either measure the headspace gas or liquid medium inside the disposable bioreactor. Additionally, these measurements can utilize any part of the electromagnetic spectrum including ultra-violet, visible, near infrared, and mid infrared to far infrared radiation or RF and DC electrical fields to probe the biochemical or chemical system inside the reactor bag. Optically, the measurements can also be done using Raman Stokes or anti-Stokes radiation, using FTIR methods, auto-fluorescence, photo-acoustic or near field optical systems to obtain the data of interest. Other measurements can involve miniaturized or on-chip: mass spectrometry, liquid chromatography, flow cytometry, or nuclear magnetic resonance (NMR). This data can be directly or indirectly indicative of the state of the bioreactor medium. Virtually any transduction method that can be used with the port of the present invention, and can be directly correlated to an analyte of interest allows for a useful sensor.

In addition to more traditional disposable bag bioreactors having rockers (Wave Biotech) or mixers (Hyclone, XCellerex) or spargers (e.g., air-lift) for agitation, other types of bioreactors including those disposable bioreactors that utilize hollow fibers, or parallel plates for growth (e.g.: Corning Cell Cube®) can benefit from the use of the port and disposable probe technology of the present invention. Finally, given that our technology is conceptually also compatible with standard ports on glass and metal bioreactors, the present invention can also be utilized with non-disposable bioreactors.

BRIEF DESCRIPTION OF THE DRAWINGS

FIG. 2 shows a port assembly allowing for a variety of optical, electrical, acoustic, magnetic, and micro-fluidic measurements to take place in a disposable bioreactor.

FIG. 3 shows a port combined with a patch of material to facilitate attachment of the port to the wall of the bioreactor vessel.

FIG. 4 shows a port and sensor assembly where a disposable optical gap is used for the purpose of monitoring total cell density. This system can also be used for spectroscopic measurements.

FIG. 5 shows a port and sensor assembly where near-infrared and mid-infrared radiation is used in conjunction with an attenuated total reflection spectroscopy system. This assembly can be used to detect multiple analytes simultaneously.

FIG. 6 shows a port and sensor assembly adapted for use with an optical fiber based phase fluorometric or Raman measurement systems.

FIG. 7 shows a port and sensor assembly adapted for use with free space optics based phase fluorometric measurement systems.

FIG. 8 shows a port and sensor assembly adapted for use with electrical sensors such as ion specific field effect transistors, or conductivity, temperature, or osmolality sensors.

DETAILED DESCRIPTION OF THE INVENTION

Figure 1:
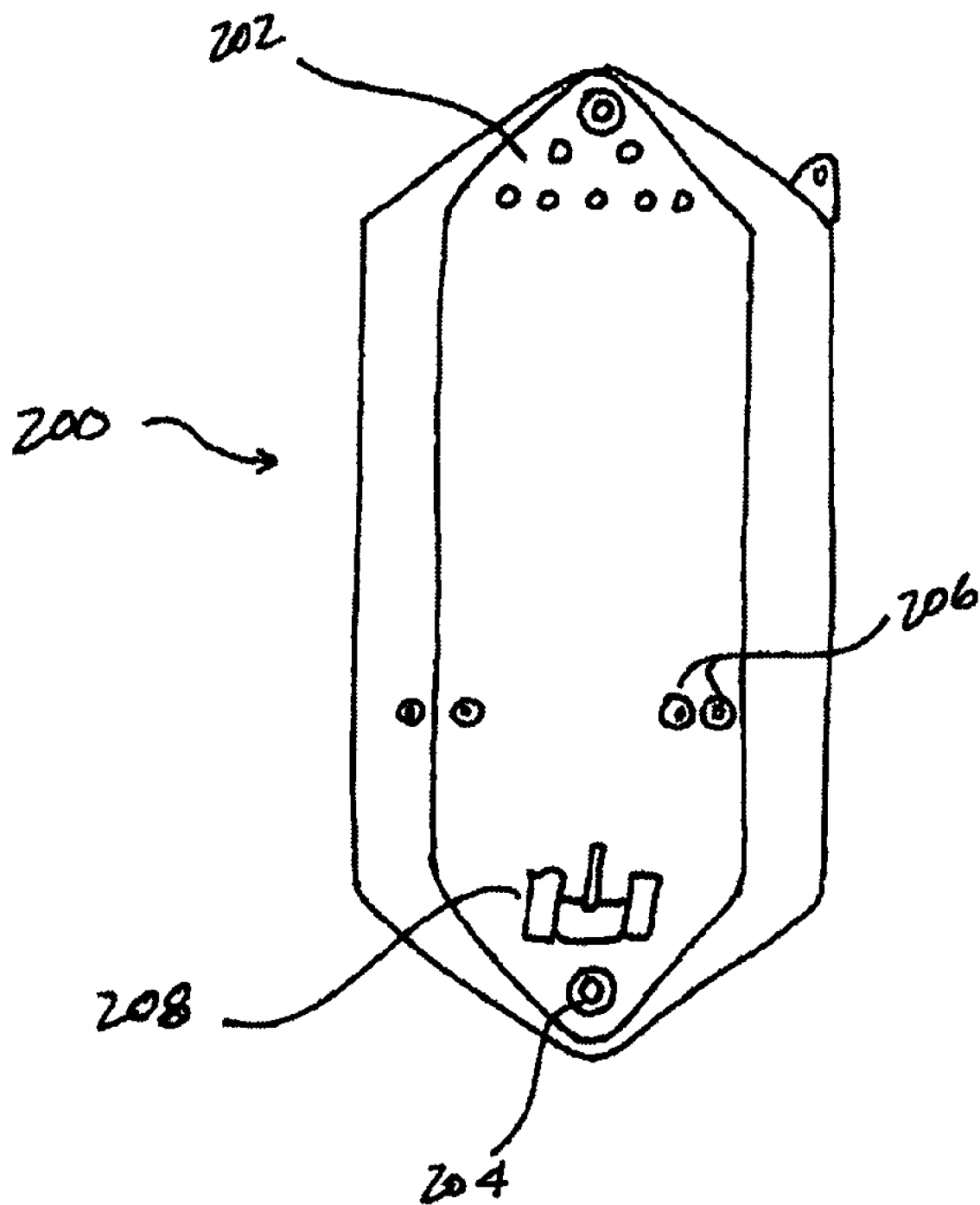
FIG. 1 shows a disposable bioreactor bag in accordance with the prior art.
Figure 2:
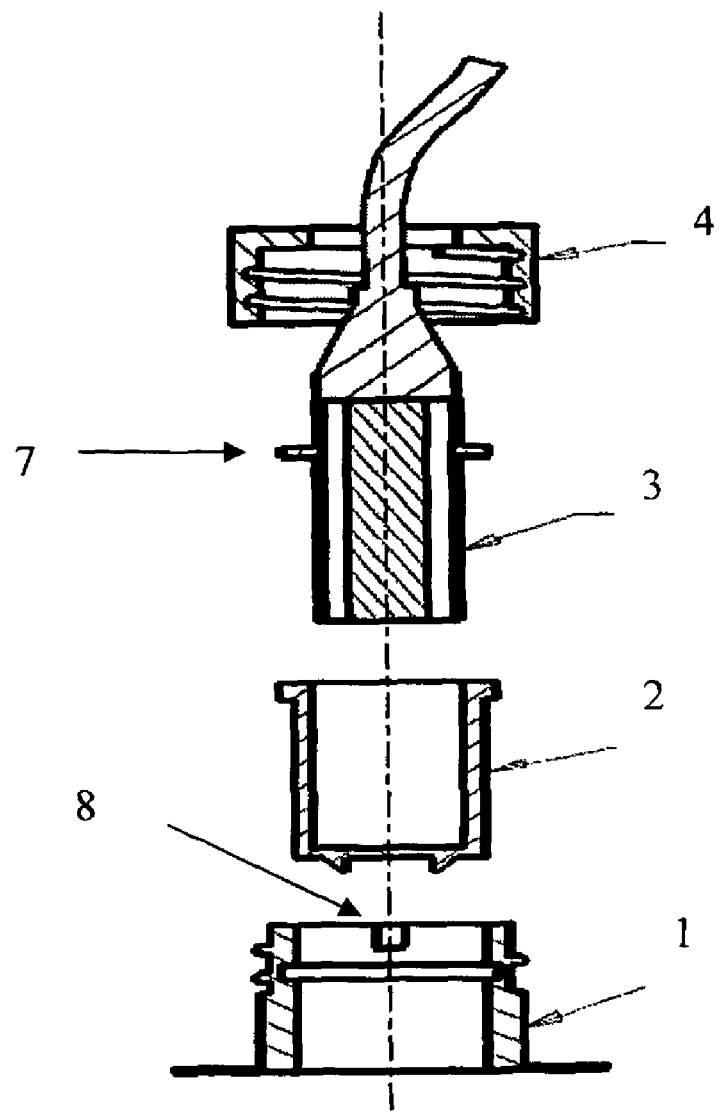
FIGS. 2 through 8 illustrate various embodiments in accordance with the present invention.

Ports for use with a syringe to draw material out of a disposable bioreactor bag or to inject material into a bag are known but such ports are suitable only to remove or introduce fluid into the bioreactor and are not designed for use with advanced monitoring sensors, and are clearly not suitable to support the use of ecumenical probes. We have developed a solution for the monitoring of critical analytes in the liquid medium contained in a disposable bioreactor by placing a sealable port in the wall of the disposable bioreactor. One embodiment of our unique design of a port for analytical use is shown in FIG. 2. The analytical port of the present invention can accommodate a variety of optical, electrical, acoustic, magnetic, and/or micro-fluidic platforms for monitoring and control applications. FIG. 2 is a cross-sectional drawing which depicts how this port functions. In FIG. 2, 1 designates a portion of the port that can be permanently affixed to the disposable bioreactor's lining by RF or heat welding it to the bag. This port component serves as a base plate and can be made of either rigid material (e.g. polyethylene) in order to provide structural integrity of an inserted subsystem, or can be made of a flexible material (e.g.: a cyclo-olefin) to conform to a more delicate subsystem that does not require support. Also shown is an insertable bushing element 2 that can facilitate a variety of measurements. In its simplest form it can contain a passive optical component that simply directs light from and back to 3, (the "reader"), through the fluid on the inside of the bioreactor. Reader 3, can be an optical, electrical, acoustic, magnetic, or micro-fluidic (or combination) system which holds the appropriate infrastructure for the measurement. Such infrastructure can comprise an optical source and a photo-detector which measures the signal emanating from a dye spot present on component 3 and/or the extent of absorption of light transmitted across an optical gap to thereby determine the absorption caused by the bioreactor fluid. Further embodiments of this insert will be discussed in connection with other figures illustrating the invention. Note that the reader can be constructed from metal or rigid plastics (e.g. an aromatic polyether-ketone) and does not come in contact with the contents of the disposable bioreactor. The reader can, but is not necessarily held in by a cap or locking mechanism 4. Threads are shown in FIG. 2, but alternative retention methods or: arrangements that retain the system in a fixed position can be utilized. For example, the reader can be attached to the disposable insert by a mechanical spring loaded or threaded pin, while the disposable insert is held to the port for example by using a tie wrap or a compression ring. Also, depending on the material system chosen, the disposable insert can be bonded or permanently affixed to the port. The monitoring assembly can be keyed so as to permit insertion into said bushing in only one orientation. In FIG. 2 pins 7 on monitoring element 3 engage notches 8 to determine the insertion orientation. The notches are also shown as 9 in FIG. 3.

Figure 3:
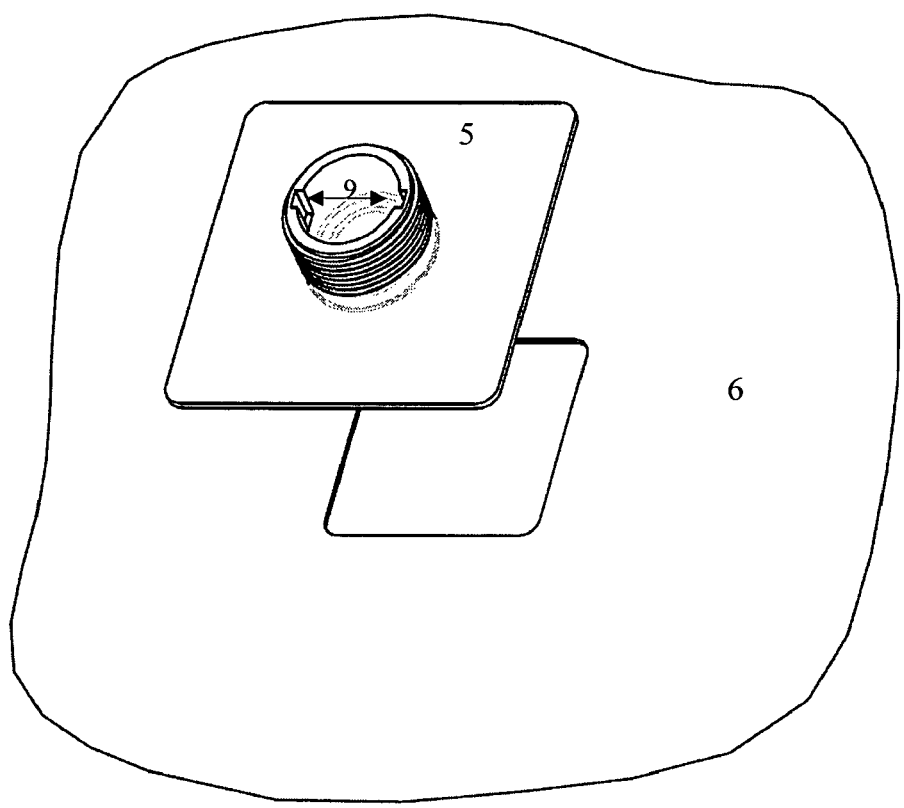

FIG. 3 shows an overview of how a disposable port in accordance with the present invention can be mounted to the lining 6 of a disposable bioreactor. The port base portion (5) can be sealed to lining 6 using known methods including, but not limited to RF energy, a thermal source, and acoustic/ultrasonic energy.

Figure 4:
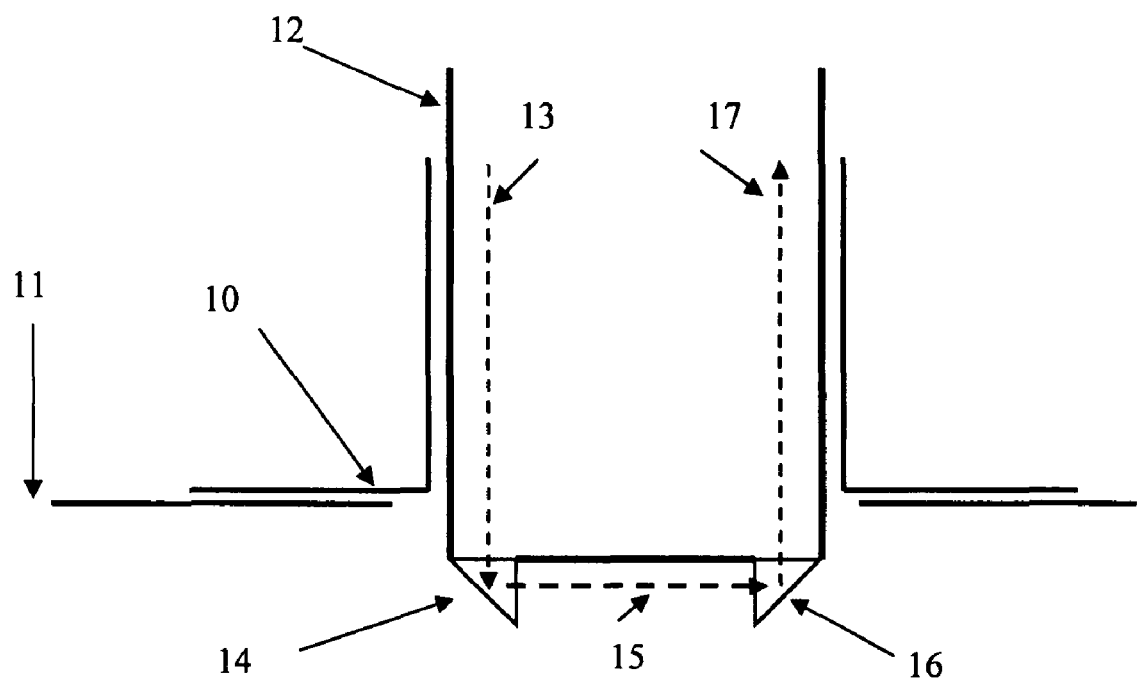

FIG. 4 shows an embodiment of the port assembly shown generally in FIG. 2 when designed for monitoring cell density. The port structure 10 (corresponding to element 1 in FIG. 2) is affixed to the lining 11 of the disposable bioreactor. A normally disposable element 12 (corresponding to element 2 of FIG. 2) which is preferably made of a polymeric material that can be sterilized using gamma or beta radiation, and which meets FDA and USP requirements for biocompatibility is inserted into the port. This element 12 has substantially optically transparent sections or can house optical elements 14 and 16. These elements are used to create an optical gap 15 which is immersed in the bioreactor fluid. The appropriate source light 13 (e.g.: a diode laser, an appropriately spectrally filtered LED, a diode pumped solid state laser etc.) is coupled to the optics and traverses the optical gap 15 and returns 17 to the photo-detector (not shown) for signal processing. This type of cell density sensor is known to those skilled in the art (see, for example, U.S. Pat. No. 7,180,594). It should also be noted that with the appropriate optical source and appropriate detection optics and electronics, the system shown in FIG. 4 can also be used to identify analytes through the use of direct transmission or absorption spectroscopy, or Raman spectroscopy (e.g.: Andrew Berger, Tae-Woong Koo, Irving Itzkan, Gary Horowitz, and Michael S. Feld, *Multicomponent blood analysis by near-infrared Raman spectroscopy*, Applied Optics, 38, 13, 1999, p. 2916). The embodiment shown in FIG. 4 can also be used for the detection of auto-fluorescence, or for use in direct UV absorption measurements to quantify protein and amino acid purity, concentration, as well aid in metabolic monitoring (e.g.: Simon C. W. Kwong and Govind Rao, *Metabolic Monitoring by Using the Rate of Change of NAD(P)H Fluorescence, Biotechnology and Bioengineering*, Vol. 44, No. 4, Aug. 5, 1994, p. 454). The embodiment shown in FIG. 4 can also be adapted to cavity enhanced type measurements (e.g.: B. A. Paldus, et al., Cavity ring-down spectroscopy using mid-infrared quantum cascade lasers, Optics Letters 25, 2000, p. 666) by utilizing appropriate optics. A reader, which is connected to a transmitter, is not shown here. The reader holds the optics and electronics necessary to enable each of the aforementioned measurements and is inserted into the disposable insert 12 as described in connection with FIG. 2. The optical or electronic signals are then displayed on the transmitter.

Figure 5:
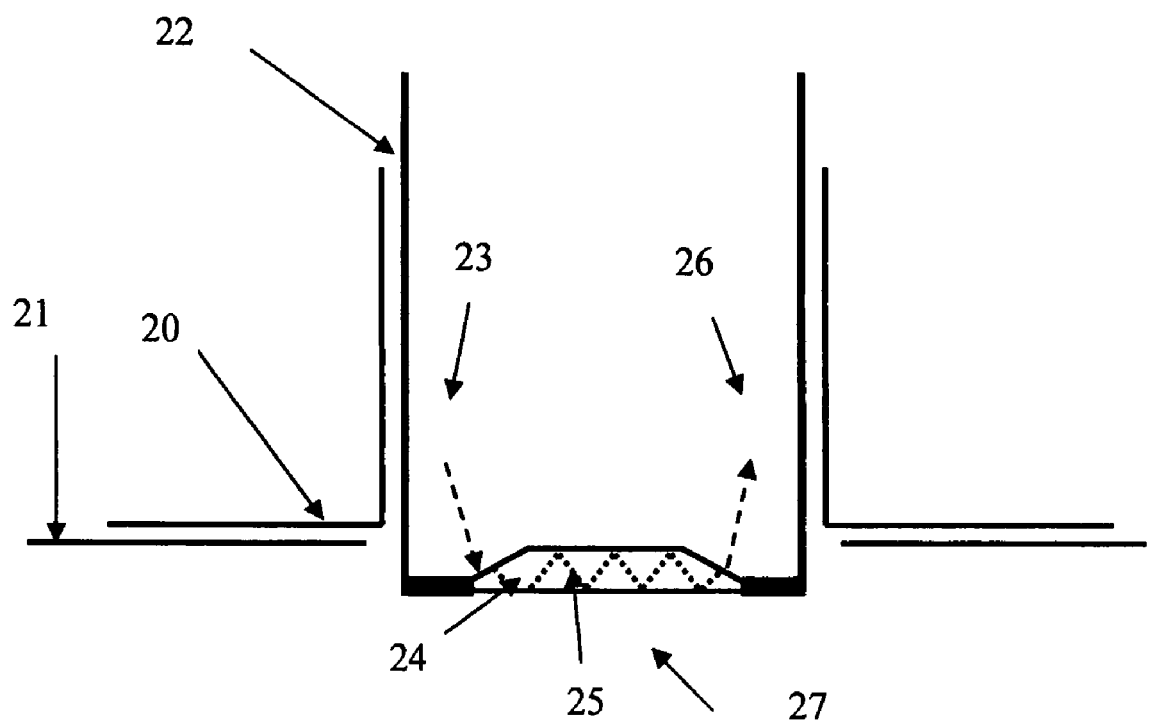

In FIG. 5 an alternative design another assembly is shown where port 20 (corresponding to element 1 in FIG. 2) is affixed to the disposable bioreactor's lining 21. A biocompatible insert 22 (corresponding to element 2 of FIG. 2) is provided. This insert houses passive optical elements that can be used, for example, for attenuated total reflection (ATR) spectroscopy or other variants such as evanescent wave CRDS (e.g.: A. C. R. Pipino et al, Evanescent wave cavity ring down spectroscopy with a total internal reflection mini-cavity, Review of Scientific Instruments 68, 1997, p. 2978. ATR spectroscopy is a surface sensitive absorption spectroscopy method that can be used to detect small amounts of a substance close to an interface. In the ATR geometry shown in FIG. 5, the input radiation 23 is totally internally reflected at the interface 24 to the bioreactor fluid 27. At each bounce site there is an evanescent field that can extend a few microns into the fluid and is absorbed if anything in the bioreactor has a transition at the wavelengths of illumination. The effects of this absorption are contained in the output radiation 26. The Ge, ZnSe, Chalcogonide glass, or other materials used can be constructed as a zig-zag slab 25 as shown in FIG. 5, or can be as simple as an optical fiber.

As mentioned previously, it is possible to utilize optically based sensors in order to monitor dissolved oxygen, pH, and dissolved CO2 as well as other key bioreactor analytes. One optical method is fluorometry, in particular phase fluorometry. Details on fluorescence spectroscopy and phase fluorometry can be found in J. Lakowicz, *Principles of Fluorescence Spectroscopy*, 2$^{nd}$ Edition, Kluwer Academic/Plenum Press, 1999. Fluorometric detection systems can be adapted to use a port and sensor assembly of the present invention as illustrated in FIG. 6.

Figure 6:
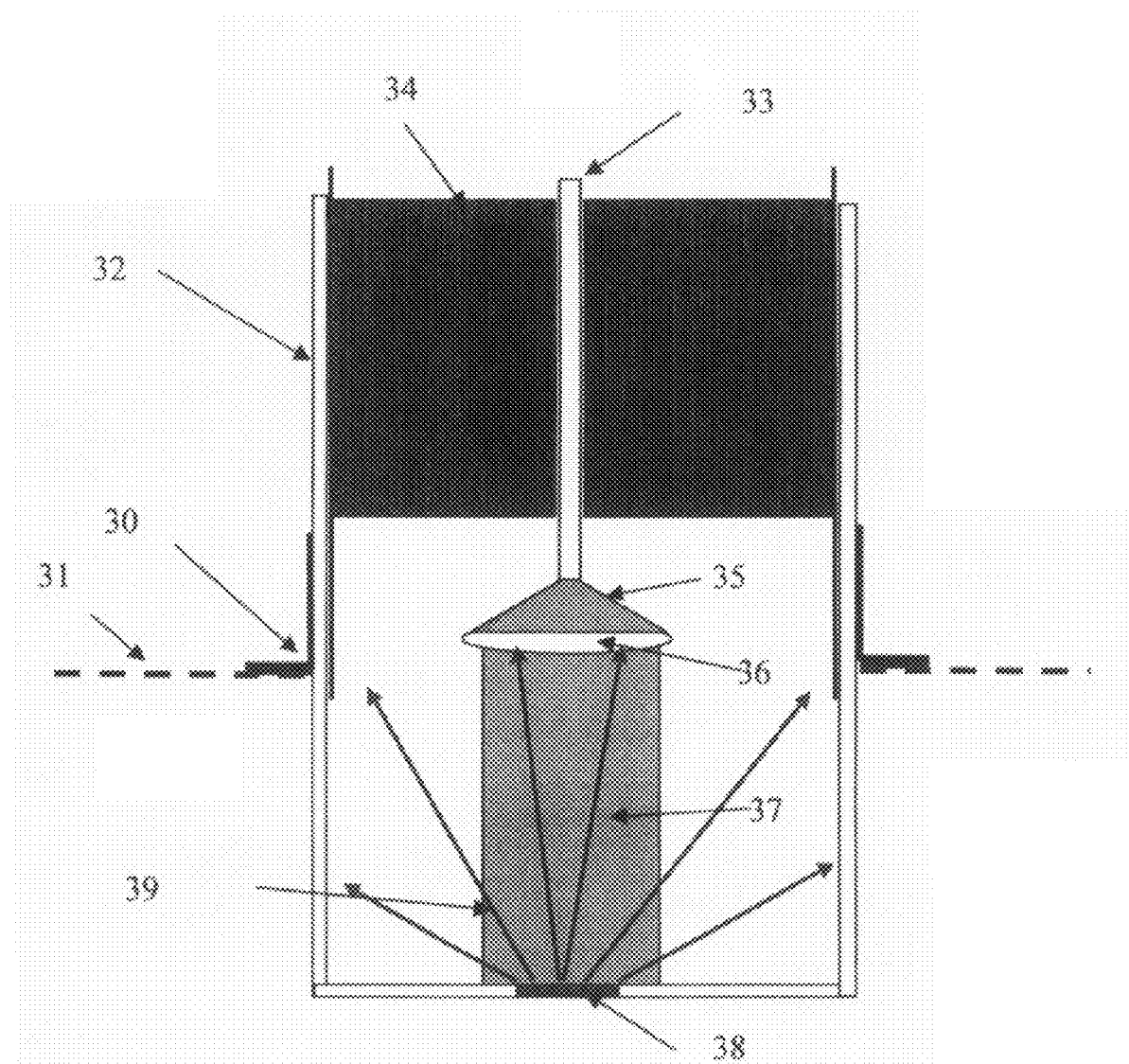

In FIG. 6, use of a fiber or fiber bundle 33 as the excitation light source is shown. The fiber system is anchored into the disposable insert shell 32 (corresponding to element 2 of FIG. 2) through a ferrule 34 or other suitable retention system. The diverging light 35 from the fiber or fiber bundle will preferably be collimated using a lens or lens system 36. Use of such a lens system enables the collimated light 37 to be precisely incident on the fluorescent dye spot 38. If the excitation light is not collimated, it will continue to impinge on the fluorescent dye spot but will provide general illumination of the area rather than a focused beam incident precisely upon the fluorescent dye spot. The fluorophore absorbs the excitation light and then emits fluorescent light 39. This fluorescent signal then impinges upon the collection system, shown here as lens 36, and is focused 35 and returns to a photo-diode (not shown) through the fiber or fiber bundle 33. Note that the lens system 36 and optic fiber 33 is suitable to focus and transmit both the illuminating light and the fluorescent signal. The fluorescent dye spot and fiber in FIG. 6 are also mounted in disposable shell 32 which is preferably comprised of a USP and FDA regulation compliant material, which is optically transparent and moldable or machinable. This disposable shell is shown inserted into port 30 (corresponding to element 1 in FIG. 2) that is affixed to the disposable bioreactor's lining 31.

Figure 7:
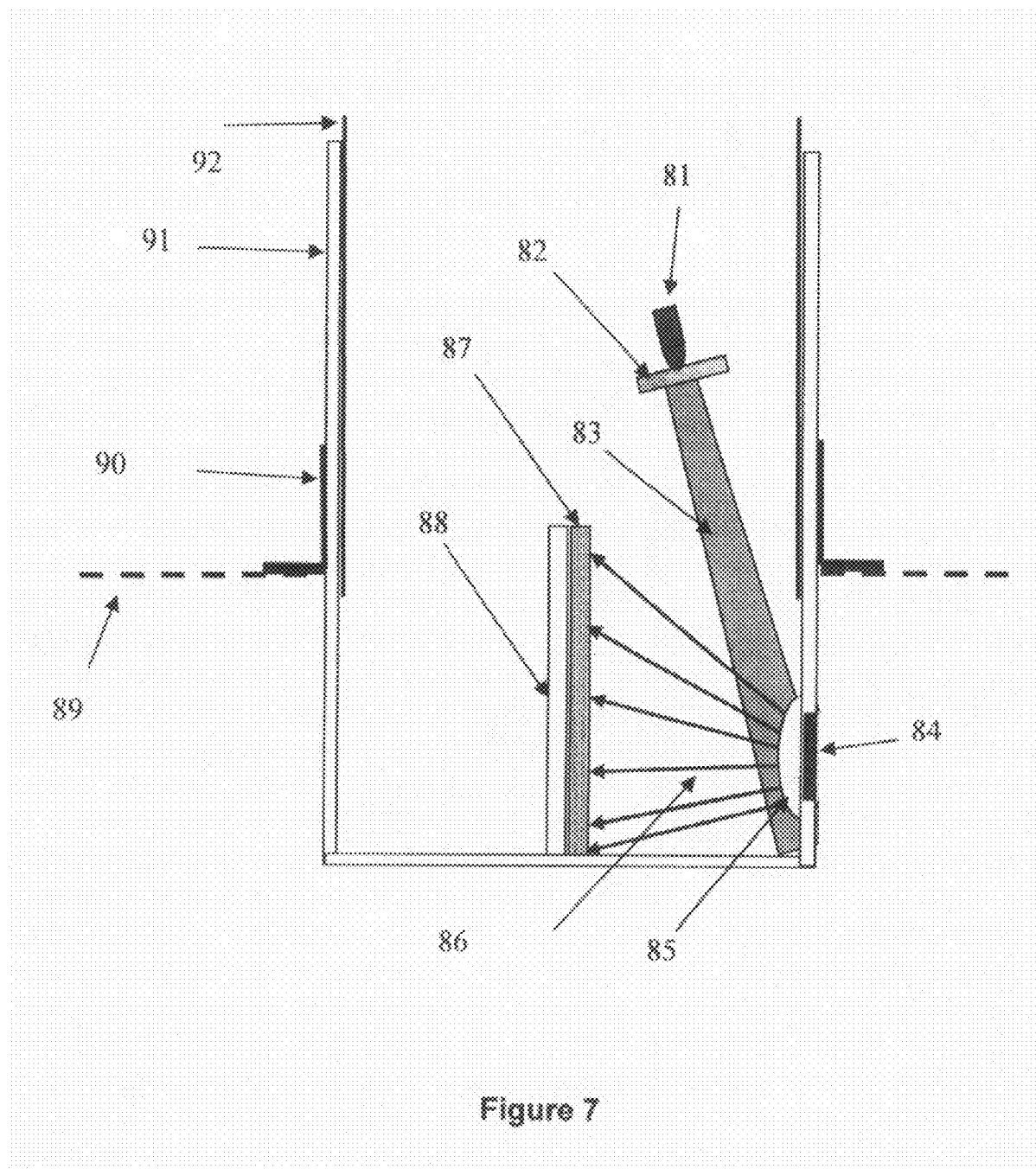

FIG. 7 shows another port and sensor assembly in accordance with the present invention for use with fluorometric analyte detection systems. In FIG. 7, the optical assembly will preferably be permanently attached to the reader whose housing 92 inserts into the disposable shell 91 (corresponding to element 2 of FIG. 2) which is inserted into port 90 (corresponding to element 1 in FIG. 2). The reader will typically contain an excitation light source 81 which is preferably an LED. The LED spectrum is narrowed by an optical filter 82 which passes that part of the optical beam 83 whose wavelength is matched to the absorption spectrum of the fluorophore (fluorescent material spot) 84. The fluorescent signal 86 is collected by an appropriate optical system 85. The collected signal fluorescent signal passes through a second optical filter 87 which allows substantially only the fluorescent signal to pass, and blocks any other light from impinging on the photodetector 88.

Figure 8:
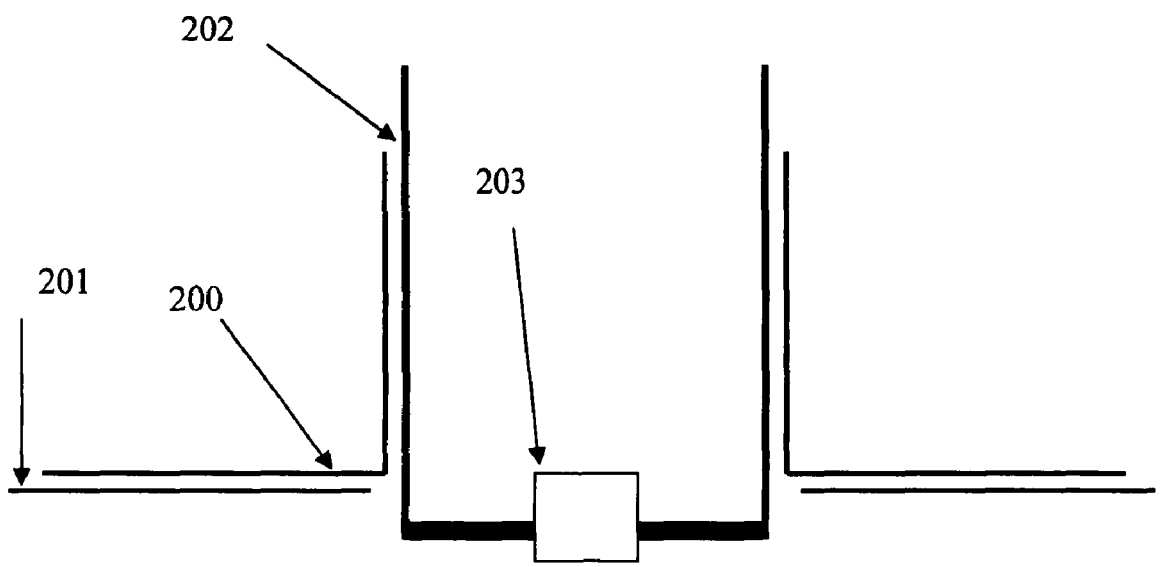

FIG. 8 shows a port and sensor assembly where 200 indicates the port (corresponding to element 1 in FIG. 2) which is affixed to the disposable bioreactor lining 201. The preferably biocompatible and USP and FDA compliant insert 202 (corresponding to element 2 of FIG. 2) is shown holding an ion specific field effect transistor 203 (ISFET, see for example:

However, any any chemFET or other measuring apparatus for, temperature, conductivity, or osmolality can be employed using this configuration of assembly.

Figure 9:
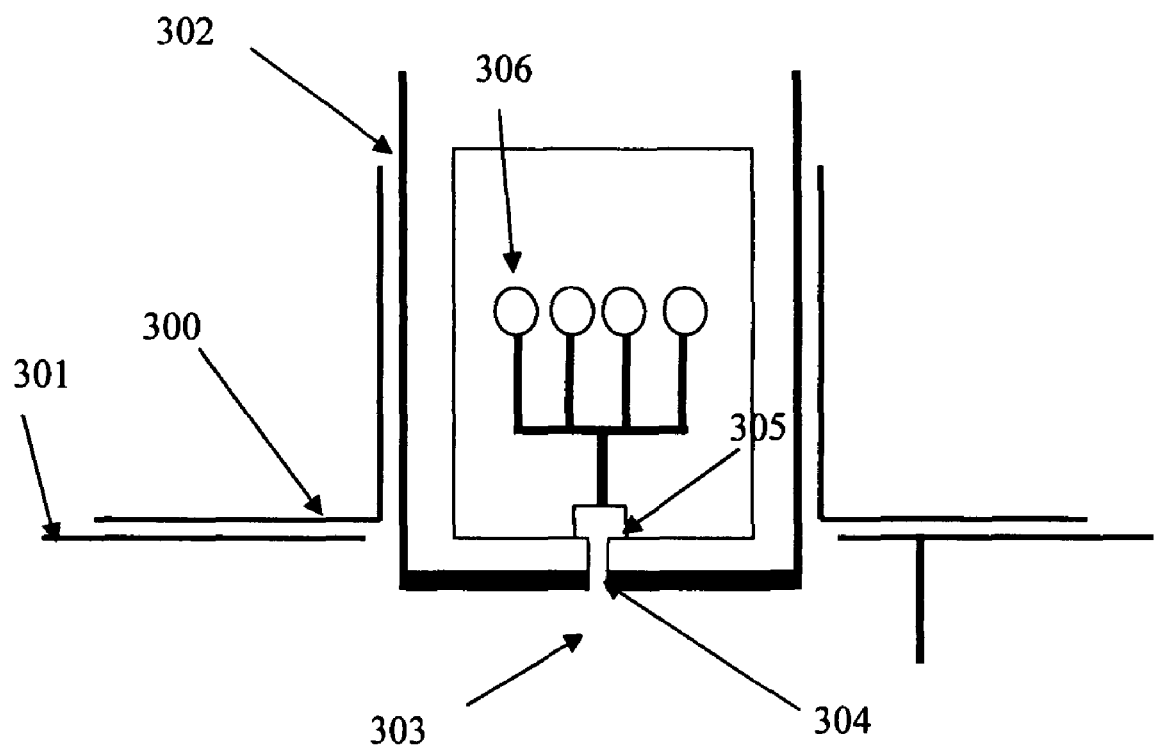
FIG. 9 shows a port in accordance with the present invention and a microfluidic sensor allowing a lab-on-chip sensor such as a miniaturized flow cytometer, mass spectrometer or liquid chromatograph.

The use of a port also enables the ability to easily connect to an auto-sampler or to utilize micro-fluid cards and readers is shown in FIG. 9. For instance, through use of the aforementioned port, a combination optical/micro-fluid device for in-line and/or at-line flow cytometry, liquid chromatography, mass spectrometry, NMR, or reagent basic chemical analysis is feasible. Through the use of sampling techniques, many standard enzymatic reactions can be utilized to determine analyte concentrations. For example, glucose, lactate, glutamine, glutamate concentrations can be determined through such enzymatic reactions. Additionally, at-line flow cytometry can be applied to determine cell viability or phenotype using the port assembly shown in FIG. 9. As long as there is access to the bioreactor fluid, and a valve system to avoid back flow contamination standard flow cytometry systems can be applied. In FIG. 9, 300 is the actual port, 301 is the lining of the disposable reactor, 302 is an insert that is made of a biocompatible material. This insert is in contact with the bioreactor's fluid 303, and has an opening 304 with a valve 305 such that fluid can only exit the bioreactor. The bioreactor fluid can be mixed with an enzyme to test for various analytes, and the waste material is stored in reservoirs 306 on the chips.

The invention claimed is:
1. A port for use with a bioreactor vessel, said port comprising:
  i) a base member comprising a flexible hollow tubular portion and a base plate, said base plate being fusibly sealable to the wall of said bioreactor vessel at a hole therein;
  ii) a hollow, partially transparent generally tubular bushing member for containing electrical, and/or optical monitoring components which bushing member fits inside the bore of the tubular portion of said base member, said bushing member providing access to the contents of said bioreactor vessel and being comprised of a bioreactor compatible polymeric material suitable for sterilization by γ or β radiation;
  iii) a monitoring assembly inserted into said bushing member which assembly comprises means for providing incoming optical and/or electrical signals and means for collecting and transmitting measurement signals resulting from the interaction of said incoming optical and/or electrical signals with the contents of said bioreactor wherein said monitoring assembly is keyed so as to permit insertion into said bushing in only one orientation; and iv) a retainer to maintain the position and alignment of the monitoring assembly.

2. The port of claim 1 wherein said monitoring assembly measures at least one of temperature, pH, pressure, and/or the concentration of one or more of dissolved $O_2$, $CO_2$, ammonia, glutamine, and lactic acid present in said bioreactor vessel.

3. The port of claim 1 wherein said monitoring assembly measures the concentration of at least one of glucose, amino acid, cholesterol, vitamin and protein.

4. The port of claim 1 wherein said monitoring assembly measures cell density and/or cell viability.

5. The port of claim 1 wherein said monitoring assembly permits removal of a micro-fluidic sample for analysis by mass spectrometry, nuclear magnetic resonance, or liquid chromatography.

6. The port of claim 1 wherein said monitoring assembly enables two or more measurements to be made simultaneously from said port.

7. The port of claim 6 where said two or more measurements include fluorometric pH/DO, or ATR detection of glucose/lactate.

8. The port of claim 1 wherein said retainer is a threaded cap which maintains the position of said monitoring assembly relative to said base member.

9. The port of claim 1 wherein said monitoring assembly components are electrical and/or optical.

* * * * *